(12) United States Patent
Romoda et al.

(10) Patent No.: US 9,095,413 B2
(45) Date of Patent: Aug. 4, 2015

(54) INTRAOCULAR SHUNT MANUFACTURE

(71) Applicant: AqueSys, Inc., Aliso Viejo, CA (US)

(72) Inventors: Laszlo O. Romoda, San Clemente, CA (US); Brian Hamstrom, Trabuco Canyon, CA (US); Partha Chandrakant, Foothill Ranch, CA (US); Christopher Horvath, Desert Hot Springs, CA (US)

(73) Assignee: AqueSys, Inc., Aliso Viejo, CA (US)

( * ) Notice: Subject to any disclaimer, the term of this patent is extended or adjusted under 35 U.S.C. 154(b) by 0 days.

(21) Appl. No.: 14/295,022

(22) Filed: Jun. 3, 2014

(65) Prior Publication Data
US 2014/0287077 A1 Sep. 25, 2014

Related U.S. Application Data

(62) Division of application No. 13/314,950, filed on Dec. 8, 2011, now Pat. No. 8,765,210.

(51) Int. Cl.
*B05C 3/12* (2006.01)
*A61F 9/007* (2006.01)

(52) U.S. Cl.
CPC ............. *A61F 9/00781* (2013.01); *B05C 3/12* (2013.01)

(58) Field of Classification Search
CPC ....................................................... B05C 3/12
USPC .................... 118/56, 400, 404, 405, 422, 423
See application file for complete search history.

(56) References Cited

U.S. PATENT DOCUMENTS

| | | | |
|---|---|---|---|
| 3,788,327 A | 1/1974 | Donowitz et al. | |
| 3,960,150 A | 6/1976 | Hussain et al. | |
| 4,090,530 A | 5/1978 | Lange | |
| 4,431,688 A * | 2/1984 | Kornmann | 427/310 |
| 4,562,463 A | 12/1985 | Lipton | |
| 4,583,117 A | 4/1986 | Lipton et al. | |
| 4,722,724 A | 2/1988 | Schocket | |
| 4,744,362 A | 5/1988 | Grundler | |
| 4,750,901 A | 6/1988 | Molteno | |
| 4,787,885 A | 11/1988 | Binder | |
| 4,804,382 A | 2/1989 | Turina et al. | |
| 4,820,626 A | 4/1989 | Williams et al. | |
| 4,826,478 A | 5/1989 | Schocket | |
| 4,848,340 A | 7/1989 | Bille et al. | |
| 4,863,457 A | 9/1989 | Lee | |
| 4,902,292 A | 2/1990 | Joseph | |
| 4,911,161 A | 3/1990 | Schechter | |
| 4,915,684 A | 4/1990 | MacKeen et al. | |

(Continued)

FOREIGN PATENT DOCUMENTS

GB 2 296 663 A 7/1996
WO WO 94/13234 A1 6/1994

(Continued)

*Primary Examiner* — Cachet Sellman
(74) *Attorney, Agent, or Firm* — Nathan S. Smith; McDermott Will & Emery LLP (57) ABSTRACT

An intraocular shunt can be manufactured using a system that includes a liquid bath and a wire, which is moved through the bath. When moved through the bath, the wire is coated with a material, such as gelatin. For example, the liquid bath can have a top layer, including water, and a bottom layer, including gelatin. The coated wire passes through an aperture formed in a plate component of the system. The gelatin can be dried on the wire in a humidity-controlled space, thereby forming the shunt.

20 Claims, 5 Drawing Sheets

(56) References Cited

U.S. PATENT DOCUMENTS

| | | | |
|---|---|---|---|
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Fedorov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,178,604 A | 1/1993 | Baerveldt et al. |
| 5,180,362 A | 1/1993 | Worst |
| 5,201,750 A | 4/1993 | Hocherl et al. |
| 5,275,622 A | 1/1994 | Lazarus et al. |
| 5,290,295 A | 3/1994 | Querals et al. |
| 5,300,020 A | 4/1994 | L'Esperance, Jr. |
| 5,338,291 A | 8/1994 | Speckman et al. |
| 5,342,370 A | 8/1994 | Simon et al. |
| 5,360,339 A | 11/1994 | Rosenberg |
| 5,368,015 A | 11/1994 | Wilk |
| 5,370,607 A | 12/1994 | Memmen |
| 5,399,951 A | 3/1995 | Lavallee et al. |
| 5,410,638 A | 4/1995 | Colgate et al. |
| 5,443,505 A | 8/1995 | Wong et al. |
| 5,476,445 A | 12/1995 | Baerveldt et al. |
| 5,516,522 A | 5/1996 | Peyman et al. |
| 5,520,631 A | 5/1996 | Nordquist et al. |
| 5,545,206 A | 8/1996 | Carson |
| 5,558,629 A | 9/1996 | Baerveldt et al. |
| 5,558,630 A | 9/1996 | Fisher |
| 5,601,094 A | 2/1997 | Reiss |
| 5,665,093 A | 9/1997 | Atkins et al. |
| 5,665,114 A | 9/1997 | Weadock et al. |
| 5,670,161 A | 9/1997 | Healy et al. |
| 5,688,562 A | 11/1997 | Hsiung |
| 5,695,474 A | 12/1997 | Daugherty |
| 5,704,907 A | 1/1998 | Nordquist et al. |
| 5,722,948 A | 3/1998 | Gross |
| 5,743,868 A | 4/1998 | Brown et al. |
| 5,763,491 A | 6/1998 | Brandt et al. |
| 5,868,697 A | 2/1999 | Richter et al. |
| 5,908,449 A | 6/1999 | Bruchman et al. |
| 5,928,424 A * | 7/1999 | Krebs et al. ............... 118/405 |
| 5,932,299 A | 8/1999 | Katoot |
| 6,007,511 A | 12/1999 | Prywes |
| 6,007,578 A | 12/1999 | Schachar |
| 6,050,970 A | 4/2000 | Baerveldt |
| 6,102,045 A | 8/2000 | Nordquist et al. |
| 6,165,210 A | 12/2000 | Lau et al. |
| 6,203,513 B1 | 3/2001 | Yaron et al. |
| 6,228,873 B1 | 5/2001 | Brandt et al. |
| 6,261,256 B1 | 7/2001 | Ahmed |
| 6,264,665 B1 | 7/2001 | Yu et al. |
| 6,280,468 B1 | 8/2001 | Schachar |
| 6,450,937 B1 | 9/2002 | Mercereau et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,638,239 B1 | 10/2003 | Bergheim et al. |
| 6,666,841 B2 | 12/2003 | Gharib et al. |
| 6,676,998 B2 * | 1/2004 | Huang et al. ............... 427/434.6 |
| 6,699,210 B2 | 3/2004 | Williams et al. |
| 6,726,664 B2 | 4/2004 | Yaron et al. |
| 6,730,056 B1 | 5/2004 | Ghaem et al. |
| 6,736,791 B1 | 5/2004 | Tu et al. |
| 6,881,198 B2 | 4/2005 | Brown |
| 6,939,298 B2 | 9/2005 | Brown et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,980 B2 | 4/2007 | Christian et al. |
| 7,291,125 B2 | 11/2007 | Coroneo |
| 7,297,154 B2 | 11/2007 | Tu et al. |
| 7,331,984 B2 | 2/2008 | Tu et al. |
| 7,344,528 B1 | 3/2008 | Tu et al. |
| 7,431,709 B2 | 10/2008 | Pinchuk et al. |
| 7,431,710 B2 | 10/2008 | Tu et al. |
| 7,458,953 B2 | 12/2008 | Peyman |
| 7,488,303 B1 | 2/2009 | Haffner et al. |
| 7,524,298 B2 | 4/2009 | Gharib et al. |
| 7,594,899 B2 | 9/2009 | Pinchuk et al. |
| 7,625,384 B2 | 12/2009 | Eriksson et al. |
| 7,678,065 B2 | 3/2010 | Haffner et al. |
| 7,708,711 B2 | 5/2010 | Tu et al. |
| 7,740,604 B2 | 6/2010 | Schieber et al. |
| 7,794,437 B2 | 9/2010 | Humayun et al. |
| 7,837,644 B2 | 11/2010 | Pinchuk et al. |
| 7,862,531 B2 | 1/2011 | Yaron et al. |
| 7,867,186 B2 | 1/2011 | Haffner et al. |
| 7,998,497 B2 | 8/2011 | de Juan, Jr. et al. |
| 8,003,124 B2 | 8/2011 | Varner et al. |
| 8,109,896 B2 | 2/2012 | Nissan et al. |
| 8,267,882 B2 | 9/2012 | Euteneuer et al. |
| 8,277,437 B2 | 10/2012 | Saal et al. |
| 8,308,701 B2 | 11/2012 | Horvath et al. |
| 8,313,454 B2 | 11/2012 | Yaron et al. |
| 8,337,393 B2 | 12/2012 | Silvestrini et al. |
| 8,337,509 B2 | 12/2012 | Schieber et al. |
| 8,377,122 B2 | 2/2013 | Silvestrini et al. |
| 8,425,449 B2 | 4/2013 | Wardle et al. |
| 8,444,589 B2 | 5/2013 | Silvestrini |
| 8,486,000 B2 | 7/2013 | Coroneo |
| 8,506,515 B2 | 8/2013 | Burns et al. |
| 8,512,404 B2 | 8/2013 | Frion et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 2002/0099434 A1 | 7/2002 | Buscemi et al. |
| 2002/0133168 A1 | 9/2002 | Smedley et al. |
| 2002/0143284 A1 | 10/2002 | Tu et al. |
| 2003/0015203 A1 | 1/2003 | Makower et al. |
| 2003/0055372 A1 | 3/2003 | Lynch et al. |
| 2003/0060752 A1 | 3/2003 | Bergheim et al. |
| 2003/0097151 A1 | 5/2003 | Smedley et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0077987 A1 | 4/2004 | Rapacki et al. |
| 2004/0111050 A1 | 6/2004 | Smedley et al. |
| 2004/0147870 A1 | 7/2004 | Burns et al. |
| 2004/0154946 A1 | 8/2004 | Solovay et al. |
| 2004/0216749 A1 | 11/2004 | Tu |
| 2004/0225250 A1 | 11/2004 | Yablonski |
| 2004/0254521 A1 | 12/2004 | Simon |
| 2004/0260227 A1 | 12/2004 | Lisk, Jr. et al. |
| 2005/0049578 A1 | 3/2005 | Tu et al. |
| 2005/0119601 A9 | 6/2005 | Lynch et al. |
| 2005/0143363 A1 | 6/2005 | De Juan et al. |
| 2005/0246023 A1 | 11/2005 | Yeung |
| 2005/0250788 A1 | 11/2005 | Tu et al. |
| 2005/0261624 A1 | 11/2005 | Wilcox |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0032507 A1 | 2/2006 | Tu |
| 2006/0106370 A1 | 5/2006 | Baerveldt et al. |
| 2006/0110428 A1 | 5/2006 | De Juan et al. |
| 2006/0116625 A1 | 6/2006 | Renati et al. |
| 2006/0147643 A1 * | 7/2006 | Volkov et al. ............... 427/431 |
| 2006/0149194 A1 | 7/2006 | Conston et al. |

(56) References Cited

U.S. PATENT DOCUMENTS

| | | |
|---|---|---|
| 2006/0155238 A1 | 7/2006 | Shields |
| 2006/0173397 A1 | 8/2006 | Tu et al. |
| 2006/0173446 A1 | 8/2006 | Dacquay et al. |
| 2006/0200113 A1 | 9/2006 | Haffner et al. |
| 2007/0118065 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | de Juan, Jr. et al. |
| 2007/0233037 A1 | 10/2007 | Gifford, et al. |
| 2007/0269487 A1 | 11/2007 | de Juan, Jr. et al. |
| 2007/0293807 A1 | 12/2007 | Lynch et al. |
| 2007/0293872 A1 | 12/2007 | Peyman |
| 2008/0108933 A1 | 5/2008 | Yu et al. |
| 2008/0147001 A1 | 6/2008 | Al-Marashi et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0082860 A1 | 3/2009 | Schieber et al. |
| 2009/0082862 A1 | 3/2009 | Schieber et al. |
| 2009/0099626 A1 | 4/2009 | de Juan, Jr. et al. |
| 2009/0104243 A1 | 4/2009 | Utkhede et al. |
| 2009/0177138 A1 | 7/2009 | Brown et al. |
| 2009/0182421 A1 | 7/2009 | Silvestrini et al. |
| 2009/0209910 A1 | 8/2009 | Kugler et al. |
| 2009/0287136 A1 | 11/2009 | Castillejos |
| 2010/0100104 A1 | 4/2010 | Yu et al. |
| 2010/0114006 A1 | 5/2010 | Baerveldt |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0191103 A1 | 7/2010 | Stamper et al. |
| 2010/0241046 A1 | 9/2010 | Pinchuk et al. |
| 2011/0046536 A1 | 2/2011 | Stegmann et al. |
| 2011/0098627 A1 | 4/2011 | Wilcox |
| 2011/0098809 A1 | 4/2011 | Wardle et al. |
| 2011/0105986 A1 | 5/2011 | Bronstein et al. |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2011/0319806 A1 | 12/2011 | Wardle |
| 2012/0078362 A1 | 3/2012 | Haffner et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123435 A1 | 5/2012 | Romoda et al. |
| 2012/0123436 A1 | 5/2012 | Reitsamer et al. |
| 2012/0123437 A1 | 5/2012 | Horvath et al. |
| 2012/0123438 A1 | 5/2012 | Horvath et al. |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2012/0310137 A1 | 12/2012 | Silvestrini |
| 2012/0323159 A1 | 12/2012 | Wardle et al. |
| 2013/0149429 A1 | 6/2013 | Romoda et al. |
| 2013/0150770 A1 | 6/2013 | Horvath et al. |
| 2013/0150773 A1 | 6/2013 | Hertz et al. |
| 2013/0184631 A1 | 7/2013 | Pinchuk |
| 2013/0245573 A1 | 9/2013 | de Juan, Jr. et al. |
| 2013/0253406 A1 | 9/2013 | Horvath et al. |
| 2013/0253528 A1 | 9/2013 | Haffner et al. |
| 2013/0281817 A1 | 10/2013 | Schaller et al. |
| 2013/0281907 A1 | 10/2013 | Wardle et al. |
| 2013/0289467 A1 | 10/2013 | Haffner et al. |
| 2013/0325024 A1 | 12/2013 | Nissan et al. |
| 2014/0018720 A1 | 1/2014 | Horvath et al. |
| 2014/0066833 A1 | 3/2014 | Yaron et al. |
| 2014/0081195 A1 | 3/2014 | Clauson et al. |
| 2014/0180189 A1 | 6/2014 | Horvath et al. |
| 2014/0236065 A1 | 8/2014 | Romoda et al. |
| 2014/0236067 A1 | 8/2014 | Horvath et al. |
| 2014/0243730 A1 | 8/2014 | Horvath et al. |

FOREIGN PATENT DOCUMENTS

| | | |
|---|---|---|
| WO | WO 94/21205 A1 | 9/1994 |
| WO | WO 95/08310 A1 | 3/1995 |
| WO | WO 98/23237 A1 | 6/1998 |
| WO | WO 02/074052 A2 | 9/2002 |
| WO | WO 2007/087061 A2 | 8/2007 |
| WO | WO 2008/005873 A1 | 1/2008 |
| WO | WO 2008005873 A2 * | 1/2008 |

* cited by examiner

INTRAOCULAR SHUNT MANUFACTURE

CROSS-REFERENCE TO RELATED APPLICATIONS

This application is a divisional of U.S. patent application Ser. No. 13/314,950, now U.S. Pat. No. 8,765,210, filed on Dec. 8, 2011, the entirety of which is incorporated herein by reference.

BACKGROUND

1. Field of the Invention

The invention generally relates to systems and methods for making gelatin shunts.

2. Description of the Related Art

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness.

Glaucoma may be treated in a number of different ways. One manner of treatment involves delivery of drugs such as beta-blockers or prostaglandins to the eye to either reduce production of aqueous humor or increase flow of aqueous humor from an anterior chamber of the eye. Glaucoma may also be treated by surgical intervention that involves placing a shunt in the eye to result in production of fluid flow pathways between an anterior chamber of an eye and various structures of the eye involved in aqueous humor drainage (e.g., Schlemm's canal, the sclera, or the subconjunctival space). Such fluid flow pathways allow for aqueous humor to exit the anterior chamber.

A problem with implantable shunts is that they are composed of a rigid material, e.g., stainless steel, that does not allow the shunt to react to movement of tissue surrounding the eye. Consequently, existing shunts have a tendency to move after implantation, affecting ability of the shunt to conduct fluid away from the anterior chamber of the eye. To prevent movement of the shunt after implantation, certain shunts are held in place in the eye by an anchor that extends from a body of the shunt and interacts with the surrounding tissue. Such anchors result in irritation and inflammation of the surrounding tissue. Further, implanting a rigid shunt may result in the shunt causing blunt trauma upon insertion into an eye, such as producing a cyclodialysis cleft, or separation of the ciliary body from the scleral spur, creating hypotony by allowing the uncontrolled escape of aqueous humor through the cleft into the suprachoroidal space.

To address the problems associated with shunts made of rigid material, people have begun to make shunts from flexible material, such as gelatin. See for example, Yu et al. (U.S. Pat. No. 6,544,249 and U.S. Patent Application Publication No. 2008/0108933). Gelatin shunts may be reactive to pressure, and thus can be implanted without the use of anchors. Consequently, gelatin shunts will maintain fluid flow away for an anterior 5 chamber of the eye after implantation without causing irritation or inflammation to the tissue surrounding the eye. Additionally, the flexibility of a gelatin shunt prevents it from causing blunt trauma upon insertion into an eye, and thus reduces or eliminates the risk of producing a cyclodialysis cleft.

However, there are numerous issues associated with making gelatin shunts. For example, it is difficult to control and manipulate liquid gelatin, which is important in order to produce a gelatin shunt with a uniform cross-section and uniform shape along a length of the implant. Additionally, there are challenges associated with the drying process that also make it difficult to produce a gelatin shunt with a uniform cross-section and uniform shape along a length of the implant.

SUMMARY

The invention generally provides systems and methods for making gelatin shunts. Particularly, systems and methods of the invention address and solve the above-described problems with manufacturing gelatin shunts.

Certain aspects of the invention address the problems of controlling and manipulating liquid gelatin. The invention recognizes that simply routing a wire through a temperature controlled gelatin bath is not sufficient to produce a gelatin shunt with a uniform cross-section and uniform shape along a length of the implant. Heated gelatin alone forms a skin layer on top of the gelatin. Pulling a wire through a gelatin bath alone results in the wire passing through the skin layer, which makes it impractical to control the gelatin uptake on the wire. The invention solves this aspect of the problem by adding a water layer on top of the gelatin. The water layer eliminates the skin effect, and allows for production of a uniform cone of gelatin upon pulling a wire through the gelatin and then the water layer. Where the gelatin cone intersects the water-air boundary, a spot forms. This spot is exposed to air, and gelatin from this spot is taken up the wire.

However, the invention also recognizes that more gelatin reaches the top of the water than can be taken up by the wire. This results in cast-off, which renders the cone, and thus the spot at the boundary layer, unstable, i.e., the gelatin deposit is inconsistent in diameter. To solve this aspect of the problem, the systems and methods of the invention use a plate having an aperture, which aperture controls the gelatin spot. The plate having the aperture is situated in the water layer, and with the aperture plate in place, the cone of gelatin that feeds the spot is consistent and yields a uniform uptake of gelatin onto the wire.

Other aspects of the invention address the problems associated with the drying process that also make it difficult to produce a gelatin shunt with a uniform cross-section and uniform shape along a length of the implant. As the water evaporates from the gelatin on the wire, the gelatin shrinks in diameter. However, the wire constrains the gelatin from shrinking axially. If humidity is left uncontrolled, an outer skin of the gelatin dries and hardens before the gelatin has completed shrinking. This results in non-uniform cross sections and shapes along the implant length. The invention recognizes that drying the gelatin on the wire in a humidity-controlled space produces a uniform implant along the length of the wire. One manner by which this is accomplished involves immersing the gelatin in an ultrasonic fog that keeps the outer skin of the gelatin hydrated as the internal volume of the gelatin shrinks.

Systems and methods of the invention incorporate these solutions to the above-described problems associated with manufacturing a gelatin shunt. Methods of the invention may involve moving a wire through a bath including a bottom layer of liquid gelatin and a top layer of water, thereby coating the wire with gelatin, moving the gelatin-coated wire through an aperture, and drying the gelatin on the wire in a humidity-controlled space, thereby manufacturing a gelatin shunt. The dried shunt includes a uniform shape and a uniform cross-section.

Movement of the wire may be controlled manually or mechanically. In certain embodiments, the moving wire is mechanically controlled, by for example, by a stepper motor. Any method for controlling humidity may be used with methods of the invention. In particular embodiments, the humidity is controlled by drying in the presence of an ultrasonic water fog. The aperture is generally located in the water layer, and the wire is preferably moved vertically through the bath, such that the gelatin-coated wire is vertical during the drying step. In certain embodiments, the manufactured shunt is sized and dimensioned to be an intraocular shunt.

In certain embodiments, the liquid gelatin may include a drug, and thus produces shunts that may be coated or impregnated with at least one pharmaceutical and/or biological agent or a combination thereof. Any pharmaceutical and/or biological agent or combination thereof may be used with shunts of the invention. The pharmaceutical and/or biological agent may be released over a short period of time (e.g., seconds) or may be released over longer periods of time (e.g., days, weeks, months, or even years). Exemplary agents include anti-mitotic pharmaceuticals such as Mitomycin-C or 5-Fluorouracil, anti-VEGF (such as Lucintes, Macugen, Avastin, VEGF or steroids). Exemplary agents are shown in Darouiche (U.S. Pat. Nos. 7,790,183; 6,719,991; 6,558,686; 6,162,487; 5,902,283; 5,853,745; and 5,624,704) and Yu et al. (U.S. Patent Application Serial No. 2008/0108933). The content of each of these references is incorporated by reference herein its entirety.

Systems of the invention may include a motor, a wire operably coupled to the motor for movement of the wire, a temperature controllable bath, an aperture plate situated in a top portion of the bath, and an ultrasonic fogger, the system being configured such that the wire moves through the bath, through the aperture plate, and into the ultrasonic fogger. Generally, the wire initially moves down toward a bottom of the bath and then turns to move vertically out of the bath. From there, the wire moves through the aperture plate, and then the wire moves vertically through the ultrasonic fogger. Systems of the invention may also include a first camera positioned to view the wire as it moves through the aperture plate. Systems of the invention may also further include a second camera that includes software to measure the gelatin-coated wire as it passes into the fogger.

The bath may be filled with liquid gelatin and water. The liquid gelatin fills a bottom layer of the bath and the water fills a top layer of bath. In certain embodiments, the liquid gelatin includes a drug.

DETAILED DESCRIPTION

Figure 1:
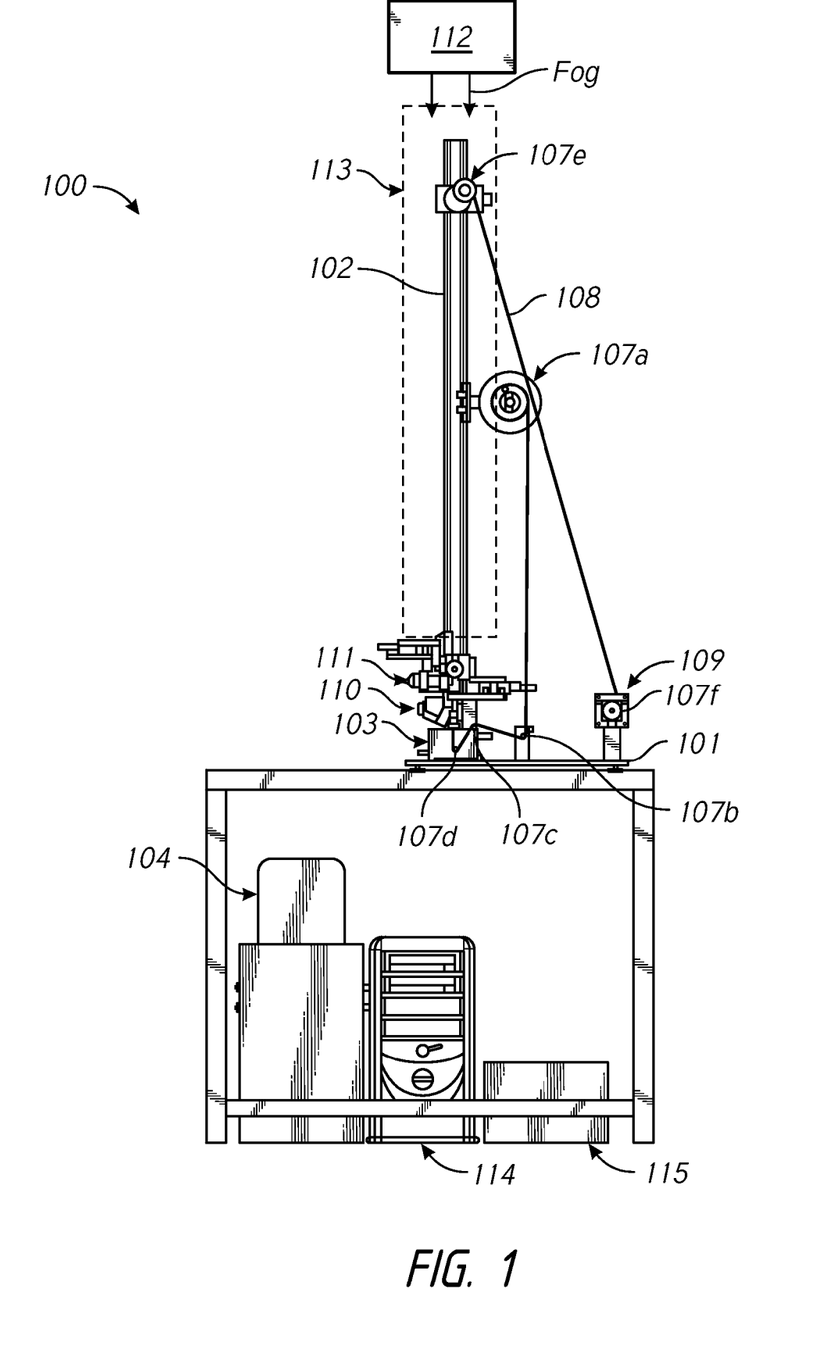
FIG. 1 is a schematic shows an embodiment of a system of the invention.

FIG. 1 shows an embodiment of a system 100 of the invention for manufacturing a gelatin shunt. Device 100 includes a base 101 and a vertically extending shaft 102. There is a bath 103 at a junction of the base 101 and the shaft 102, such that the shaft 102 is aligned with the bath 103. The bath 103 can be any vessel configured to hold a liquid. In systems of the invention, the bath 103 holds the liquid gelatin and the water. The bath is operably connected to a temperature control unit 104. The temperature control unit 104 regulates the temperature of the bath 103, and any liquids within the bath 103. For making a shunt, the bath is maintained at about 55° C.

In particular embodiments, the bath 103 is a jacketed flask and the temperature control unit 104 is a water circulator with a heating component. The heater of the temperature control unit is set to a particular temperature, for example 55° C., which heats the water in the water circulator to the set temperature. The heated water is then circulated by the water circulator to the jacked flask, which heats the flask, and its contents, to the temperature defined by the temperature control unit. Generally, the water level in the jacketed flask will be above the level of the gelatin inside the flask.

Figure 3:
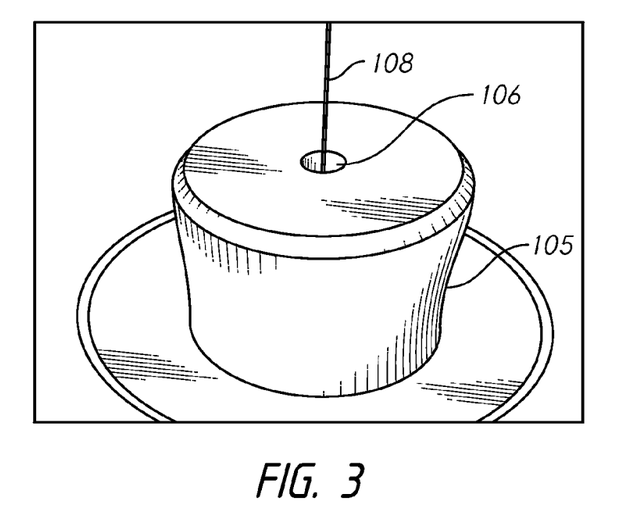
FIG. 3 is an image of the aperture plate with a wire running through the aperture.

To the top of the bath 103 is affixed an aperture plate 105, i.e., a plate having an aperture 106 therethrough. The plate 105 is affixed to the bath 103 such that the aperture 106 is aligned with the shaft 102. An exemplary shaped aperture plate 105 is shown in FIG. 3. In this figure, the plate 105 has a base portion and a protruding portion affixed to the base. The aperture runs through the base and through the protruding portion.

Figure 2:
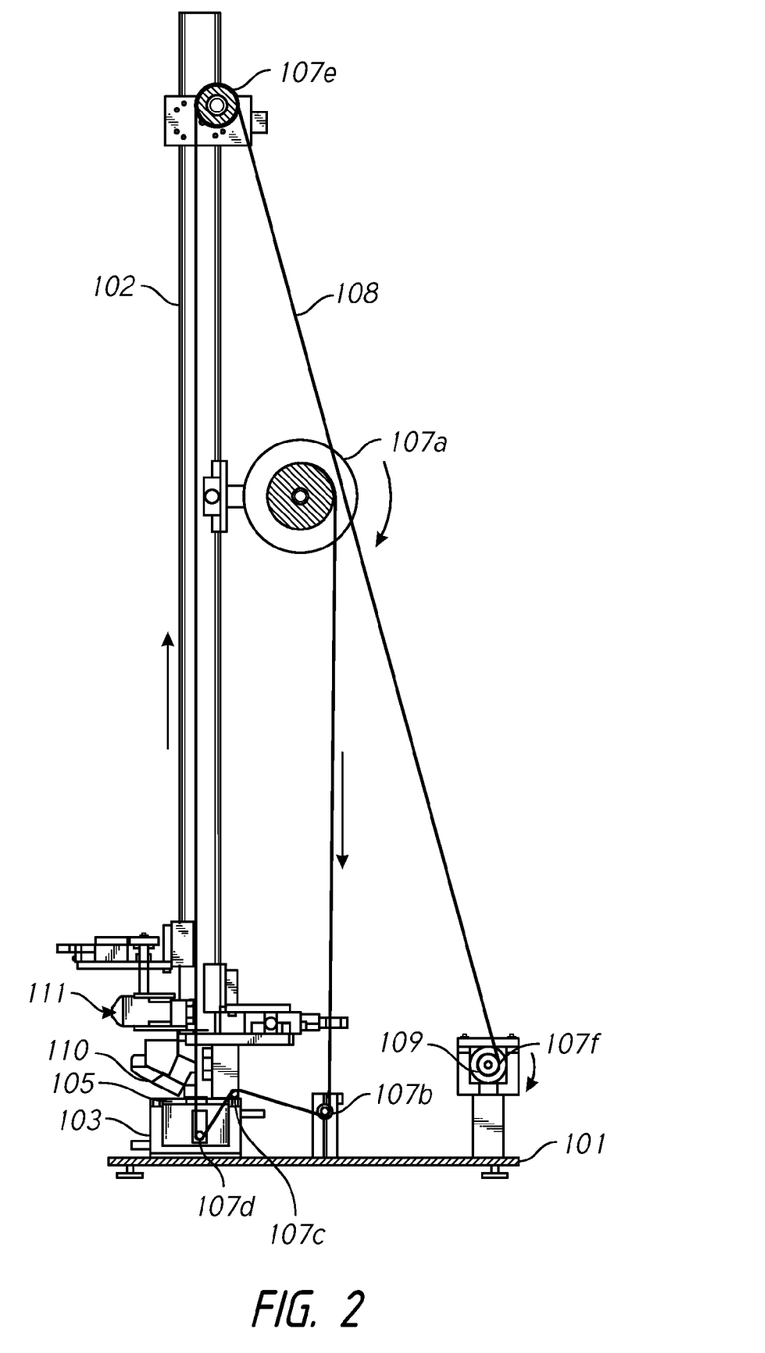
FIG. 2 is a schematic showing a magnified view of FIG. 1, focusing on the wheels that carry the wire.

System 100 includes a plurality of wheels 107. The wheels 107 support a wire 108 and are arranged in a path that the wire 108 will travel. FIG. 2 is a magnified view of the system 100 shown in FIG. 1. FIG. 2 better shows the positioning of wheels 107 and the path of travel of wire 108. Wheel 107a is mounted approximately halfway up the shaft 102. The exact position of wheel 107a on shaft 102 is not important and other positions of wheel 107a are envisioned for the systems of the invention. Wheel 107b is mounted on a support near the base 101 and is positioned to be directly below wheel 107a. Although, such exact positioning is not critical and wheel 107b may be placed in other places along the base. Wheel 107c is mounted at a top right edge of the bath 103. Wheel 107d is mounted at a bottom of bath 103. Wheel 107d is mounted such that it is in alignment with aperture 106 of aperture plate 105 and shaft 102. Wheel 107e is positioned at the top of shaft 102. The exact position of wheel 107e on shaft 102 is not important and other positions of wheel 107e are envisioned for the systems of the invention. Wheel 107f is mounted on a support near the base 101. Wheel 107f is operably coupled to stepper motor 109. An exemplary stepper motor is commercially available from Automation Direct (Cumming, Ga.).

The wheels 107 are arranged such that when wire 108 is mounted on wheels 107, the wheels provide a constant tension for wire 108. Wire 108 is spooled on wheel 107a. Wire 108 is then run under wheel 107b, over wheel 107c, under wheel 107d, over wheel 107e, and spools again onto wheel 107f. The arrangement provides that wire 108 travels down into the base of bath 103, and makes a turn at the base of bath 103, such that after the turn, wire 108 travels vertically up through the bath 103, through the aperture 106 of the aperture plate 105, and vertically up the length of the shaft 102 to wheel 107e.

Stepper motor 109 in connection with wheel 107f drives movement of wire 108 and controls the speed at which wire 108 travels. The thickness of the walls of the formed shunt will depend on the speed at which the wire 108 is traveling. Increasing the pull speed will increase the diameter of the shunt, while decreasing the pull speed will decrease the diameter of the shunt. Stepper motor 109 is controlled by computer 114 and powered by DC power supply 115.

Wire 108 is preferably stainless steel, which may optionally be coated with a biocompatible, lubricious material such as polytetrafluoroethylene (Teflon). The coating helps in removing the dried gelatin shunt from the wire 108. The gauge of the wire will depend on the desired inner diameter of the shunt being produced. Generally, wires are used that produce a shunt having an inner diameter from approximately 10 µm to approximately 250 µm, preferably from about 40 µm to about 200 µm.

Figure 4:
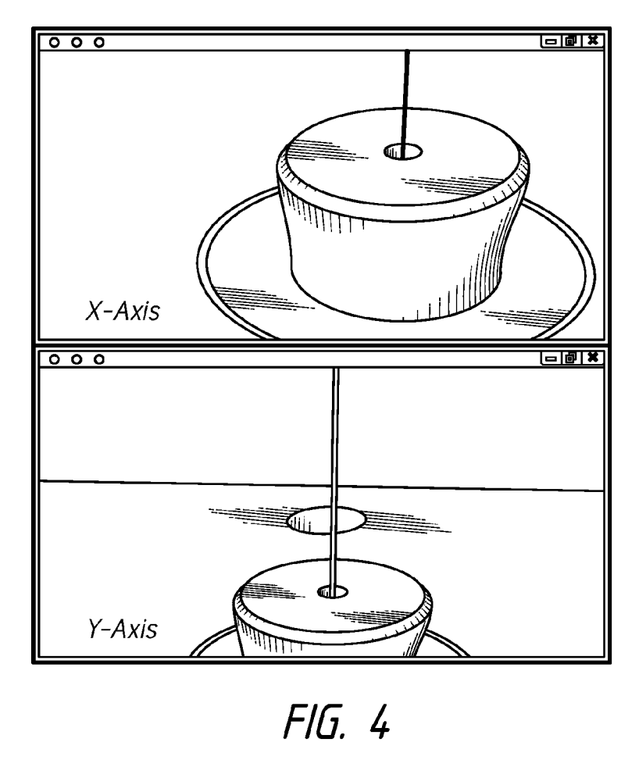
FIG. 4 shows the images captured by the first and second camera as the wire emerges from the aperture in the aperture plate.

System 100 may include at least one camera for real time monitoring of the manufacturing of the shunt. FIGS. 1-2 show an embodiment that includes two cameras 110 and 111. Camera 110 monitors the wire 108 at the point that it is emerging from the aperture 106. Camera 111 is a high magnification camera that includes measurement software to allow for real time measurement of the thickness and diameter of the gelatin coating the wire 108 as it emerges from the aperture 106. Exemplary cameras are DINO-LITE cameras, commercially available from (AnMo Electronics Corporation, Torrance, Calif.). FIG. 4 shows the images captured by cameras 110 and 111. The top image is the image produced by camera 111, and the bottom image is the image produced by camera 110). Cameras 110 and 111 are operably coupled to computer 114, which controls the cameras.

System 100 also includes an ultrasonic fogger 112 coupled to a tube 113. The tube 113 runs most of the length of the shaft 102, extending from the top of the shaft 102 down to the top camera 111. The tube 113 is positioned such that the wire 108 passes into the tube 113 upon emerging from the aperture 106. The fogger 112 is positioned such that the produced fog enters the tube 113. The fog produced by the fogger 112 keeps the outer skin of the gelatin hydrated as the internal volume of the gelatin shrinks. An exemplary fogger is commercially available from Exo-terra (Mansfield, Mass.).

To make the gelatin shunt, the bath 103 is pre-heated to a temperature of about 55° C. During the pre-heating, the liquid gelatin 116 is made. In a certain embodiment, the gelatin used for making the shunt is known as gelatin Type B from bovine skin. An exemplary gelatin is PB Leiner gelatin from bovine skin, Type B, 225 Bloom, USP. Another material that may be used in the making of the shunt is a gelatin Type A from porcine skin, also available from Sigma Chemical. Such gelatin is available from Sigma Chemical Company of St. Louis, Mo. Under Code G-9382. Still other suitable gelatins include bovine bone gelatin, porcine bone gelatin and human-derived gelatins. In addition to gelatins, the flexible portion may be made of hydroxypropyl methycellulose (HPMC), collagen, polylactic acid, polyglycolic acid, hyaluronic acid and glycosaminoglycans.

In an exemplary protocol, the gelatin solution is typically prepared by dissolving a gelatin powder in de-ionized water or sterile water for injection and placing the dissolved gelatin in a water bath at a temperature of approximately 55° C. with thorough mixing to ensure complete dissolution of the gelatin. In one embodiment, the ratio of solid gelatin to water is approximately 10% to 50% gelatin by weight to 50% to 90% by weight of water. In an embodiment, the gelatin solution includes approximately 40% by weight, gelatin dissolved in water. The resulting gelatin solution should be devoid of air bubbles and has a viscosity that is between approximately 200-500 cp and more particularly between approximately 260 and 410 cp (centipoise).

Figure 5:
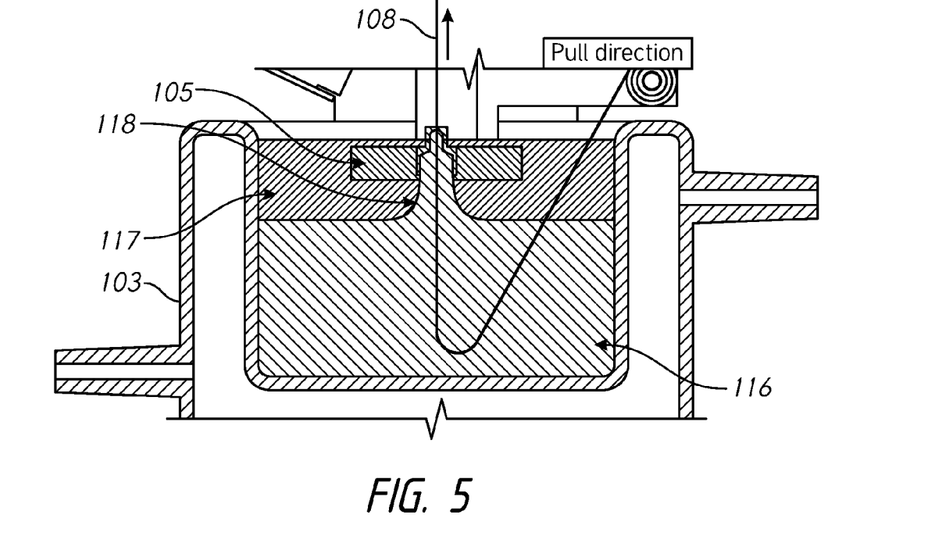
FIG. 5 is a schematic showing the wire being pulled through the gelatin and water layers and through the aperture in the aperture plate.
Figure 6:
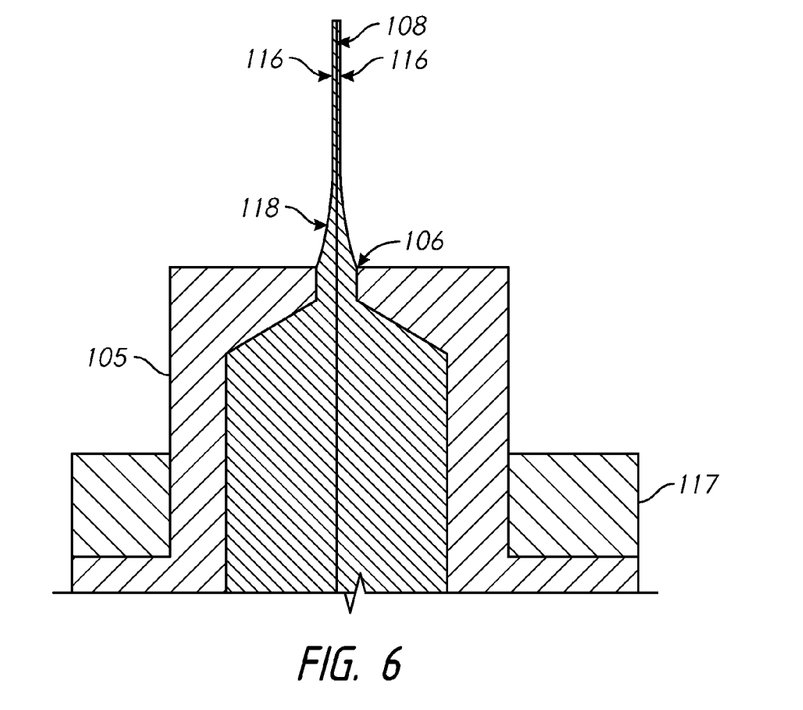
FIG. 6 is a schematic showing a magnified view of a gelatin cone interacting with the aperture plate as the wire moves through the aperture plate.

FIGS. 5 and 6 illustrate the process of the gelatin 116 being taken up the wire 108. Once prepared, the liquid gelatin 116 is poured into bath 103 that has been pre-heated to 55° C., thus maintaining the liquid gelatin at 55° C. After the gelatin 116 has been poured into the bath 103, a water layer 117 is added on top of the gelatin layer 116. The water envelops the aperture plate 105 such that a top surface of the plate 105 is submerged about 1 mm below the surface of water 117. The bottom of the plate 105 is positioned so that it does not touch the gelatin layer 116. Powered by stepper motor 109, the wire 108 is pulled down into the base of the bath 103 and then turns vertically up through the gelatin layer 116, the water layer 117, and the aperture 106 in the aperture plate 105. In this manner, the wire 108 becomes coated with gelatin 116 as it passes through the gelatin layer 116. Upon pulling the gelatin 116 through the water layer 117, a uniform cone 118 of gelatin 116 forms. Where the cone 118 intersects the water-air boundary, a spot forms. The cone 118 feeds into the aperture 106 in the aperture plate 105. The aperture 106 controls the gelatin 116 and the spot, such that the cone 118 of gelatin 116 that feeds the spot is consistent and yields a uniform uptake of gelatin 116 onto the wire 108.

The wire 108 then advances past cameras 110 and 111, which provide a real-time check of the thickness of the gelatin 116 that is being taken up the wire 108. Feedback from the camera can be used to adjust the speed of the wire 108, thus adjusting the thickness of the gelatin 116. Increasing the pull speed will increase the diameter of the shunt, while decreasing the pull speed will decrease the diameter of the shunt.

After passing the cameras, the gelatin-coated wire moves into tube 113 that is already being supplied with fog from fogger 112. The wire 108 is advanced until the wet gelatin 116 reaches the wheel 107e at the top of the shaft 102. The gelatin 116 on the wire 108 becomes immersed in the fog from fogger 112. The fogger is run for approximately 5-10 minutes after the gelatin-coated wire enters the fogger. The fogger is turned off and the gelatin is allowed to dry. Having the outer skin of the gelatin 116 in a humidity-controlled environment, keeps the skin of the gelatin 116 hydrated as an internal volume of the gelatin 116 shrinks. In this manner, a uniform implant is produced along the length of the wire 108.

The wire 108 is then cut below wheel 107e and above the top camera 111, using for example, stainless steel surgical sheers. The wire is cut into sections using the stainless steel surgical sheers to produce sections of a desired length. At this point, a cross-linking procedure can be performed on the gelatin. In one embodiment, the gelatin may be cross-linked by dipping the wire sections (with gelatin thereon) into the 25% glutaraldehyde solution, at pH of approximately 7.0-7.8 and more preferably approximately 7.35-7.44 at room temperature for at least 4 hours and preferably between approximately 10 to 36 hours, depending on the degree of cross-linking desired. In one embodiment, the gelatin is contacted with a cross-linking agent such as gluteraldehyde for at least approximately 16 hours. Cross-linking can also be accelerated when it is performed a high temperatures. It is believed that the degree of cross-linking is proportional to the bioabsorption time of the shunt once implanted. In general, the more cross-linking, the longer the survival of the shunt in the body.

The residual glutaraldehyde or other cross-linking agent is removed from the gelatin by soaking the tubes in a volume of sterile water for injection. The water may optionally be replaced at regular intervals, circulated or re-circulated to accelerate diffusion of the unbound glutaraldehyde from the gelatin. The gelatin is washed for a period of a few hours to a period of a few months with the ideal time being 3-14 days. The now cross-linked gelatin may then be dried (cured) at ambient temperature for a selected period of time. It has been observed that a drying period of approximately 48-96 hours and more typically 3 days (i.e., 72 hours) may be preferred for the formation of the cross-linked gelatin.

Where a cross-linking agent is used, it may be desirable to include a quenching agent. Quenching agents remove unbound molecules of the cross-linking agent from the gelatin. In certain cases, removing the cross-linking agent may reduce the potential toxicity to a patient if too much of the cross-linking agent is released from the gelatin. In certain embodiments, the gelatin is contacted with the quenching agent after the cross-linking treatment and, may be included with the washing/rinsing solution. Examples of quenching agents include glycine or sodium borohydride.

In certain embodiments, drug-coated/drug-impregnated shunts are produced. Shunts may be coated or impregnated with at least one pharmaceutical and/or biological agent or a combination thereof. Any pharmaceutical and/or biological agent or combination thereof may be used with shunts of the invention. The pharmaceutical and/or biological agent may be released over a short period of time (e.g., seconds) or may be released over longer periods of time (e.g., days, weeks, months, or even years). Exemplary agents include anti-mitotic pharmaceuticals such as Mitomycin-C or 5-Fluorouracil, anti-VEGF (such as Lucintes, Macugen, Avastin, VEGF or steroids). Exemplary agents are shown in Darouiche (U.S. Pat. Nos. 7,790,183; 6,719,991; 6,558,686; 6,162,487; 5,902, 283; 5,853,745; and 5,624,704) and Yu et al. (U.S. patent application serial number 2008/0108933). The content of each of these references is incorporated by reference herein its entirety.

In certain embodiments, an implant is produced with a thin layer of drug infused gelatin on an inside of the shunt. The thin inner layer will dissolve over time, thus delivering the drug. To produce such a shunt, the wire is pulled through a gelatin solution that has been infused with a drug to deposit a thin wall (e.g., 3-20 μm) of drug-infused gelatin on the wire. Alternatively, the wire is pulled through a gelatin solution that does not include a drug and the gelatin is instead soaked in the drug after it is pulled on the wire. In either case, the drug infused gelatin is then subjected to cross-linking with a controlled glutaraldehyde concentration for a controlled time to effect a non-permanent cross-linking that dissolves over time in tissue. Once this drug infused gelatin has been produced, the drug-infused gelatin is then pulled through the standard gelatin bath to coat the drug infused gelatin with a layer of gelatin that does not include a drug. This produces he final diameter of the shunt. The drug free layer of gelatin is then permanently cross-linked, thus producing a shunt with a thin layer of drug infused gelatin on an inside of the shunt.

In other embodiments, an implant is produced with a thin layer of drug infused gelatin on an outside of the shunt. The thin inner layer will dissolve over time, thus delivering the drug. To produce such a shunt, the wire is pulled through the standard gelatin solution in the bath to a diameter of about 3-50 the wire is pulled through the standard gelatin solution in the bath to a diameter of about 3-50 μm smaller than the desired diameter of the final implant. This layer is permanently cross-linked. The gelatin-coated wire is then pulled through a drug infused gelatin solution to deposit a thin wall (e.g., 3-50 μm) onto the gelatin-coated wire. Alternatively, the wire is pulled through a gelatin solution that does not include a drug and the gelatin is instead soaked in the drug after it is pulled on the wire. In either case, the drug infused gelatin is then subjected to cross-linking with a controlled glutaraldehyde concentration for a controlled time to effect a non-permanent cross-linking that dissolves over time in tissue.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLES

Example 1

Gelatin Preparation

Into a 600 mL beaker was added 98±1 grams of porcine gelatin. An amount of about 172±1 grams of USP sterile water was measured and poured into the beaker containing the porcine gelatin. The beaker was sealed with parafilm, and the covered beaker was placed in a water bath at 55±1° C. for a minimum of 8 hours (maximum 36 hours). Ensure water level is higher than mixture in beaker. The lid of the water bath was checked to ensure that it was closed and after the minimum time period had elapsed, the beaker was removed from bath. The beaker was visually observed to verify that all gelatin in the mixture was dissolved and that mixture appeared homogeneous.

Example 2

Gelatin Transfer

The water circulator was checked to make sure that it was at a sufficient level (between the high and low marks). The circulator was set and run at 40.5° C. and allowed to come to temperature before proceeding to the next step. The gelatin mixture from Example 1 was poured into the jacketed beaker on a fixture so that the meniscus was about 20 mm from the top. Within 1 minute of adding the gelatin mixture, 60 cc's of USP sterile water was added above the gelatin surface using a syringe. The water was added slowly so as not to disturb the gelatin. The mixture was allowed to settle for minimum 30 min.

Example 3

System Set-Up

Figure 7:
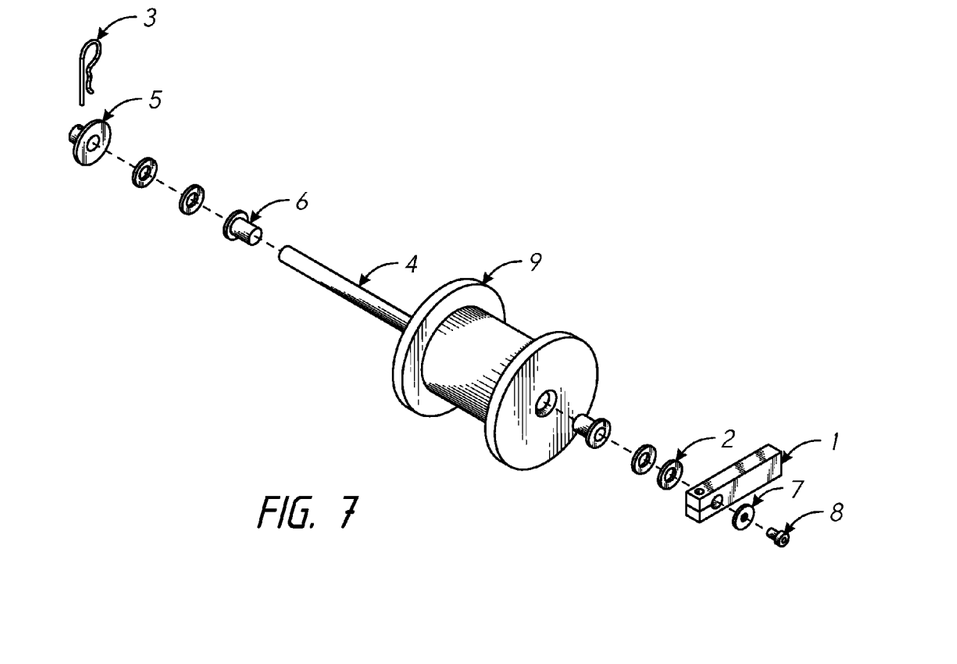
FIG. 7 is a schematic showing an exploded view of a spool.
Figure 8:
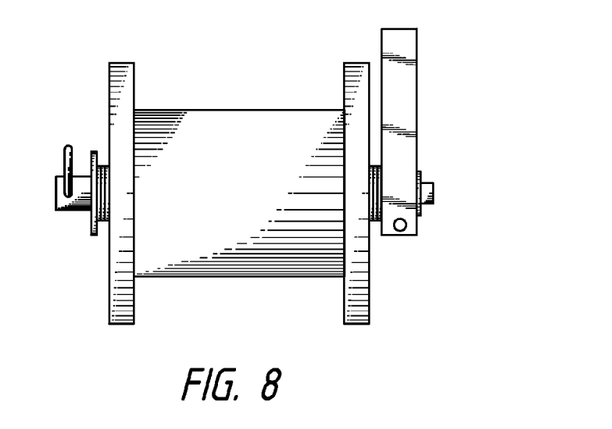
FIG. 8 is a schematic showing the final assembled spool.

A spool was assembled onto an axle using parts as shown in FIG. 7. The final assembled spool is shown in FIG. 8. The M6 screw (Item 8) was finger tightened, and pinch bolt (Item 7) was fastened onto the mount. In order to increase the friction on the spool, the M6 screw (Item 8) was advanced approximately a ¼ turn. The wire was then threaded onto the spool, and the spool was slid up the shaft. The spindle assembly was lowered into the gelatin mixture, about 5 mm from the bottom of flask. The aperture plate was lowered into the water layer under a top surface was submerged about 1 mm below the surface of water. The bottom surface of the aperture plate was above the gelatin layer.

The first and second cameras were positioned on the shaft so as to properly view the wire as it emerged from the aperture in the aperture plate. The tube of the fogger assembly was lowered over the shaft until a bottom of the tube is positioned just above the second camera. In this position, a top of the tube was approximately 2 inches above the upper wheel on the shaft. The fogger was started, and the volume and velocity on the fogger was adjusted until the fog was barely visible flowing at the bottom of the tube. The computer was initiated and the images produced by the camera were checked to ensure proper positioning of the cameras. The cameras were focused until edges of the wire had sharp contrast.

Example 4

Shunt Manufacturing

The computer was used to initiate the stepper motor and begin pulling the wire. The initial pull speed was 8,000 rpm. The aperture was checked for dry gelatin, and any dried gelatin was cleared by grasping the wire above the top camera using a gloved hand and swirling the wire around lightly for a few seconds while monitoring the aperture cameras. The concentration of the gelatin on the wire was fine-tuned by monitoring the cameras. Turning the X-axis stage micrometer in the clockwise direction moved the wire to the right relative to the gelatin. Turning the Y-axis stage micrometer in the clockwise direction moved the wire to the left relative to the gelatin. Active measures of the gelatin thickness on the wire were taken. The total diameter of the gelatin in both the X and Y views was measured. The relative wall thickness of the gelatin on each side of the wire in both the X and Y views was obtained by measuring from the left edge of the gelatin to the left edge of the wire and from the right edge of the gelatin to the right edge of the wire. The pull speed was adjusted to achieve a target wet diameter of the gelatin.

Once the target wet diameter was achieved, the fixture was run until gelatin reached the upper wheel at the top of the shaft. The movement of the wire was stopped at this point. After terminating the movement of the wire, the fog from the fogger was allowed to continue to flow over the wire for a minimum of 5 additional minutes. After five minutes, the fogger was turned off and the gelatin was allowed to dry for a minimum of 3 additional minutes. The wire was then cut below the upper wheel and above the top camera using stainless steel surgical shears. The cut wire was then subsequently cut into 4-4.25 inch sections using stainless steel surgical shears and prepared for cross-linking. The individual sections were cross-linked. The shunts were then cut to a desired length (e.g., 2-20 mm), and each shunt was removed from the wire.

What is claimed is:

1. A system, for manufacturing a gelatin shunt, comprising:
a motor;
a wire operably coupled to the motor for movement of the wire;
a temperature controllable bath;
an aperture plate situated above a bottom portion of the bath; and
an ultrasonic fogger, positioned above the plate, for providing a fog;
wherein the system is configured such that the wire moves through the bath and the aperture plate and through the fog.

2. The system of claim 1, wherein a path of the wire extends downwardly toward a bottom of the bath and then vertically out of the bath.

3. The system of claim 1, wherein the wire moves vertically through the fog.

4. The system of claim 1, wherein the aperture plate is situated in a top portion of the bath.

5. The system of claim 1, wherein the wire moves through an aperture of the aperture plate.

6. The system of claim 5, further comprising a first camera positioned to view the wire at the aperture as the wire moves through the aperture plate.

7. The system of claim 6, further comprising a second camera and software configured to provide, based on data from the second camera, a thickness measurement of a coating on the wire.

8. The system of claim 7, further comprising a liquid gelatin filling a bottom layer of the bath and water filling a top layer of the bath.

9. A system, for manufacturing an intraocular shunt, comprising:
a container configured to hold a liquid material for forming a shunt;
a plate disposed above a bottom portion of the container, the plate comprising an aperture having a cross-sectional dimension; and
a wire, extending into the container and through the aperture, being movable relative to the bottom portion of the container;
wherein the wire can be pulled from the bottom portion through the aperture to coat the wire with a liquid material such that a cross-sectional dimension of the material is limited by the cross-sectional dimension of the aperture.

10. The system of claim 9, further comprising a motor operably coupled to the wire for driving movement of the wire through the container and aperture.

11. The system of claim 9, further comprising a temperature control unit for controlling a temperature of liquid material within the container.

12. The system of claim 9, further comprising a pulley, disposed within the container and coupled to the wire for redirecting the wire through the aperture.

13. The system of claim 12, wherein a path of the wire extends downwardly toward a bottom of the container, around the pulley, and then vertically out of the container through the aperture.

14. The system of claim 9, further comprising an ultrasonic fogger, positioned above the container, configured to emit a fog for maintaining a desired humidity for the system.

15. The system of claim 14, wherein the wire moves vertically through the fog.

16. The system of claim 9, further comprising a first camera positioned to view the wire as it moves through the aperture plate.

17. The system of claim 9, further comprising a second camera and software configured to provide, based on data from the second camera, a thickness measurement of a coating on the wire.

18. The system of claim 9, wherein the plate is disposed within the container.

19. The system of claim 18, further comprising liquid material, wherein the plate is submerged in the liquid material.

20. The system of claim 19, wherein the liquid material comprises a liquid gelatin filling a bottom layer of a bath and water filling a top layer of the bath, the plate being situated above the bottom layer.

* * * * *